United States Patent [19]

Persidsky

[11] Patent Number: 5,643,176

[45] Date of Patent: Jul. 1, 1997

[54] ENDOSCOPIC INSTRUMENT WITH VARIABLE VIEWING ANGLE

[75] Inventor: Maxim D. Persidsky, San Francisco, Calif.

[73] Assignee: Power Analytics Corporation, West Sacramento, Calif.

[21] Appl. No.: 381,806

[22] Filed: Feb. 1, 1995

[51] Int. Cl.⁶ ..................................................... A61B 1/06
[52] U.S. Cl. ........................ 600/173; 600/160; 600/176; 359/831; 359/833
[58] Field of Search ........................ 600/160, 162, 600/171, 170, 173, 175, 176, 137, 135, 105; 359/831, 833, 837, 367, 399; 385/117, 118, 119, 902

[56] References Cited

U.S. PATENT DOCUMENTS

| | | | |
|---|---|---|---|
| 3,433,219 | 3/1969 | Genevay | 359/831 X |
| 3,515,464 | 6/1970 | Peifer et al. | 359/833 |
| 3,818,902 | 6/1974 | Kinoshita et al. | 600/173 X |
| 3,856,000 | 12/1974 | Chikama | 600/173 |
| 3,880,148 | 4/1975 | Kanehira et al. | 128/6 |
| 4,140,364 | 2/1979 | Yamashita et al. | 359/367 |
| 4,398,811 | 8/1983 | Nishioka et al. | 350/506 |
| 4,515,444 | 5/1985 | Prescott et al. | 350/413 |
| 5,184,602 | 2/1993 | Anapliotis et al. | 600/173 X |
| 5,190,028 | 3/1993 | Lafferty et al. | 600/138 X |

*Primary Examiner*—Richard J. Apley
*Assistant Examiner*—Beverly M. Flanagan
*Attorney, Agent, or Firm*—Flehr, Hohbach, Test, Albritton & Herbert

[57] ABSTRACT

Endoscopic instrument having an elongated image guide adapted to be inserted through an opening in the human body. A prism is provided at one end of the image guide for directing images from a predetermined field of view through the image guide and means for. By tilting the prism relative to the image guide the field of view from which images are directed through the image guide is changed to provide continuous scanning for viewing and examining different features of internal cavities and hollow organs of the human body.

15 Claims, 3 Drawing Sheets

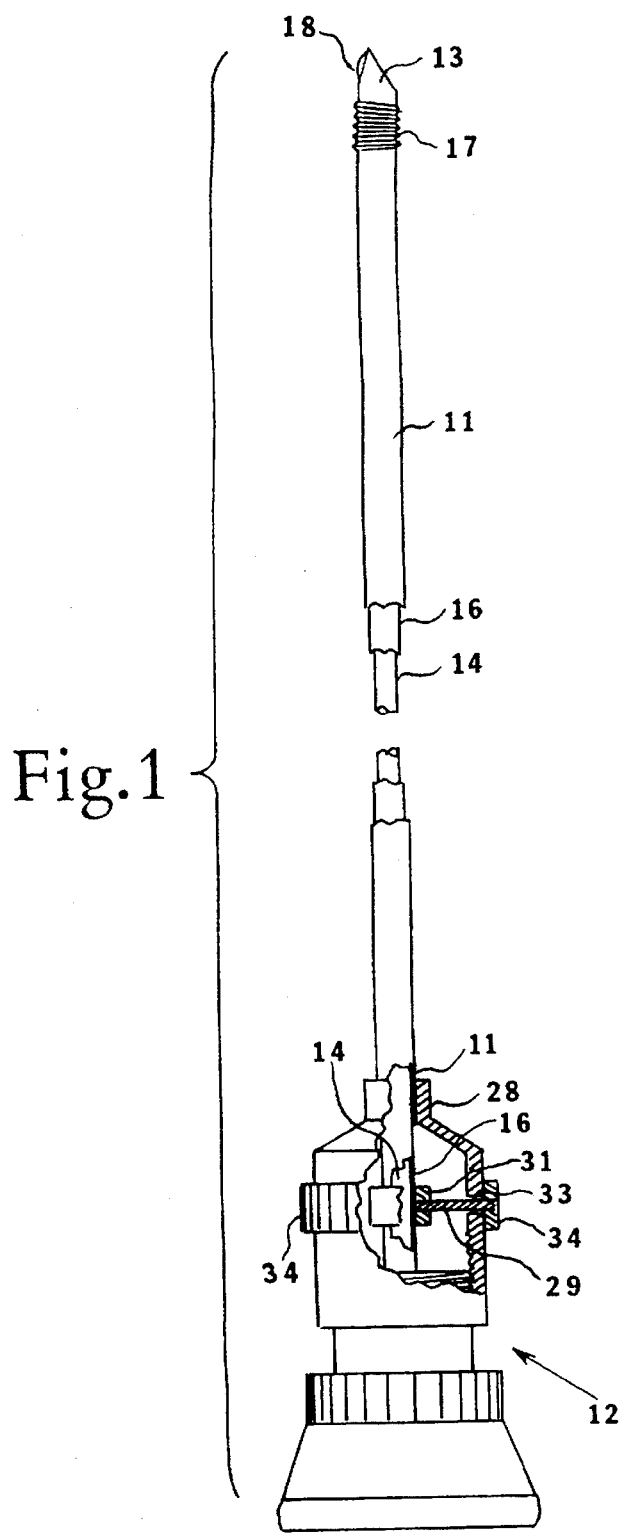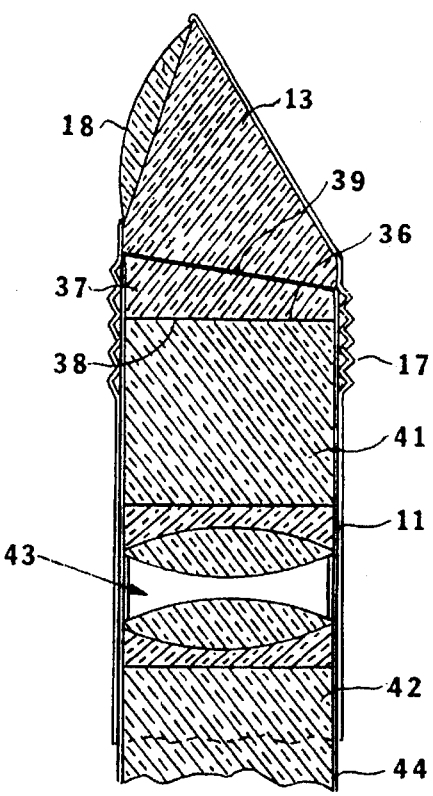

ENDOSCOPIC INSTRUMENT WITH VARIABLE VIEWING ANGLE

BACKGROUND OF THE INVENTION

1. Field of Invention

This invention pertains generally to medical instruments and, more particularly, to an endoscope for examining internal cavities and hollow organs of the human body.

2. Related Art

Endoscopes of the type commonly employed in urological applications have fixed viewing angles, with a different instrument being required for each angle desired (e.g., 90°, 70°, 45°, 30° or 0° relative to the axis of the instrument). The need to change instruments during a medical examination or surgical procedure in order to view different regions within a patient is both inconvenient for the doctor and uncomfortable for the patient, and there is always a possibility that an area of interest may be missed when the instruments are changed.

OBJECTS AND SUMMARY OF THE INVENTION

It is in general an object of the invention to provide a new and improved endoscopic instrument.

Another object of the invention is to provide an endoscopic instrument of the above character which permits continuous scanning for viewing and examining different features of internal cavities and hollow organs of the human body.

DETAILED DESCRIPTION

Another object of the invention is to provide an endoscopic instrument of the above character which eliminates the need to change instruments for different viewing angles.

These and other objects are achieved in accordance with the invention by providing an endoscopic instrument having an elongated image guide adapted to be inserted through an opening in the human body, a prism at one end of the image guide for directing images from a predetermined field of view through the image guide, and means for tilting the prism relative to the image guide to change the field of view from which images are directed through the image guide.

BRIEF DESCRIPTION OF THE DRAWINGS

FIG. 1 is a side elevational view, partly broken away, of one embodiment of an endoscope incorporating the invention.

FIG. 4 is an enlarged fragmentary sectional view of another embodiment of an endoscope incorporating the invention.

As illustrated in FIGS. 1–3, the endoscope includes an elongated outer housing 11, with an eyepiece assembly 12 at its proximal end and a prism 13 at the distal end. The housing is of tubular construction, e.g. a metal tube, and a glass rod 14 disposed within the housing serves as an image guide which transmits light from the prism to the eyepiece. The glass rod is encased in a metal sleeve 16. The instrument is of relatively small diameter and is adapted to be inserted through an opening in the human body, with the prism inside the body and the eyepiece outside.

The prism is mounted to the housing by means of a flexible bellows 17 which permits tilting of the prism relative to the glass rod to change the field of view from which light is directed to the eyepiece. In the embodiments illustrated, the bellows is fabricated of metal, and the bellows and housing are formed as a unitary structure. The prism is fabricated of a material such as cubic zirconia which has a relatively high index of refraction, and an objective lens 18 is mounted on the outer face or surface 19 of the prism.

Figure 2:
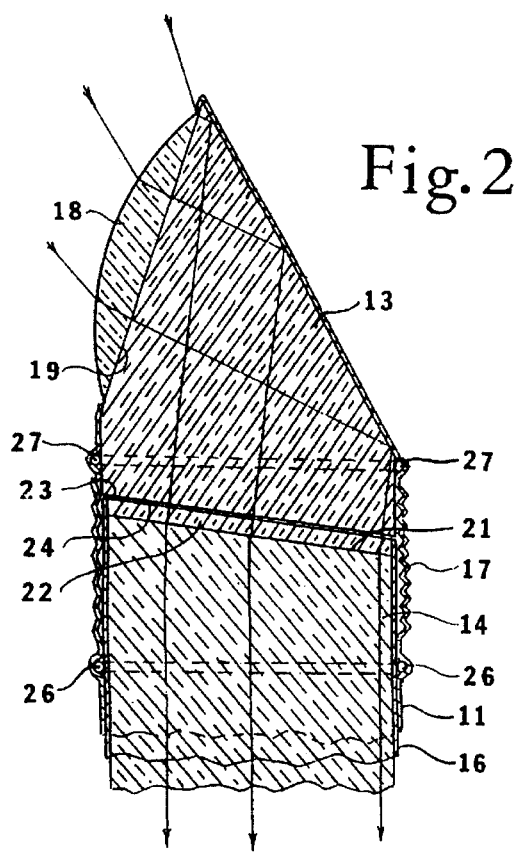
FIGS. 2 and 3 are enlarged fragmentary sectional views of the embodiment of FIG. 1 showing the prism in different operative positions.
Figure 3:
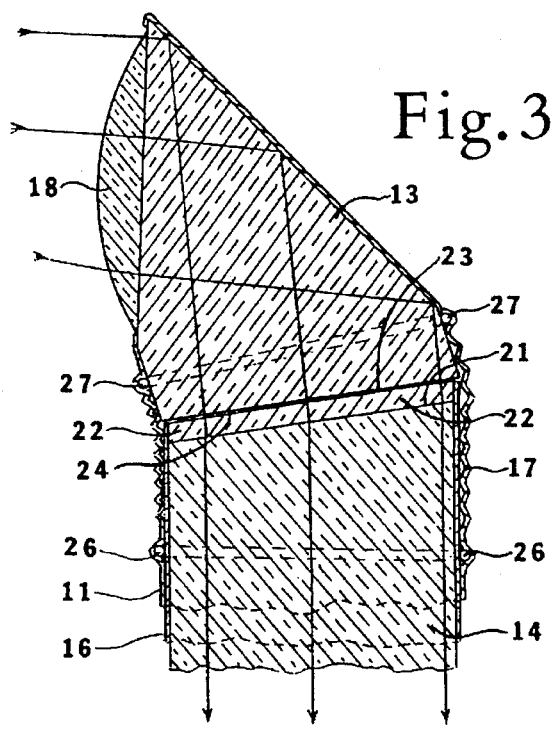

The glass rod is rotatably mounted within the housing and is utilized in tilting the prism to change the angle of view. As illustrated in FIGS. 2–3, the distal end 21 of the rod is inclined, and a thin flat plate 22 is affixed to that surface, with the outer surface 23 of the plate in rotational contact with the inner surface 24 of the prism. The plate is fabricated of the same material as the prism and prevents scratching of the relatively soft glass by the prism as might occur if the prism were in direct contact with it. With the flat plate, the outer surface of the plate is inclined at the same angle (about 80°) as the distal end of the rod. The bellows is stretched slightly, with the resiliency of the bellows maintaining the inner surface of the prism in contact with the outer surface of the plate. The joint between the rod and the prism is immersed in an optically transmissive oil which is contained within the bellows and by a pair of O-rings 26, 27 which provide seals between the bellows and the rod and prism.

As shown in FIG. 1, The eyepiece assembly includes a housing 28 which is affixed to the tubular housing 11 and has a cylindrical side wall 29 disposed concentrically of the tubular housing. A collar 31 is affixed to sleeve 16, and a pin 32 extends in a radial direction from the collar. The pin passes through a circumferentially extending slotted opening 33 in the side wall of the eyepiece housing and is connected to an operating ring 34 which is rotatively mounted on the outer wall of the housing. The opening has an arc length on the order of 180°, and the glass rod can be rotated through a corresponding angle by rotation of the ring.

The embodiment of FIG. 4 is similar to that of FIG. 1 except for the manner in which the inclined surface which tilts the prism is formed. In this embodiment, the distal end 36 of the glass rod is cut square, and a tapered plate 37 having a square-cut inner surface 38 and an inclined outer surface 39 is employed. As in the embodiment of FIG. 1, the plate is fabricated of the same material as the prism, and outer surface of the plate which engages the prism is inclined at an angle on the order of 80° to the axis of the rod.

The glass rod is formed in two sections 41, 42, with an achromatic lens assembly 43 between them. These elements are held together as a rigid unit by a metal sleeve 44 similar to sleeve 16.

Figure 5:
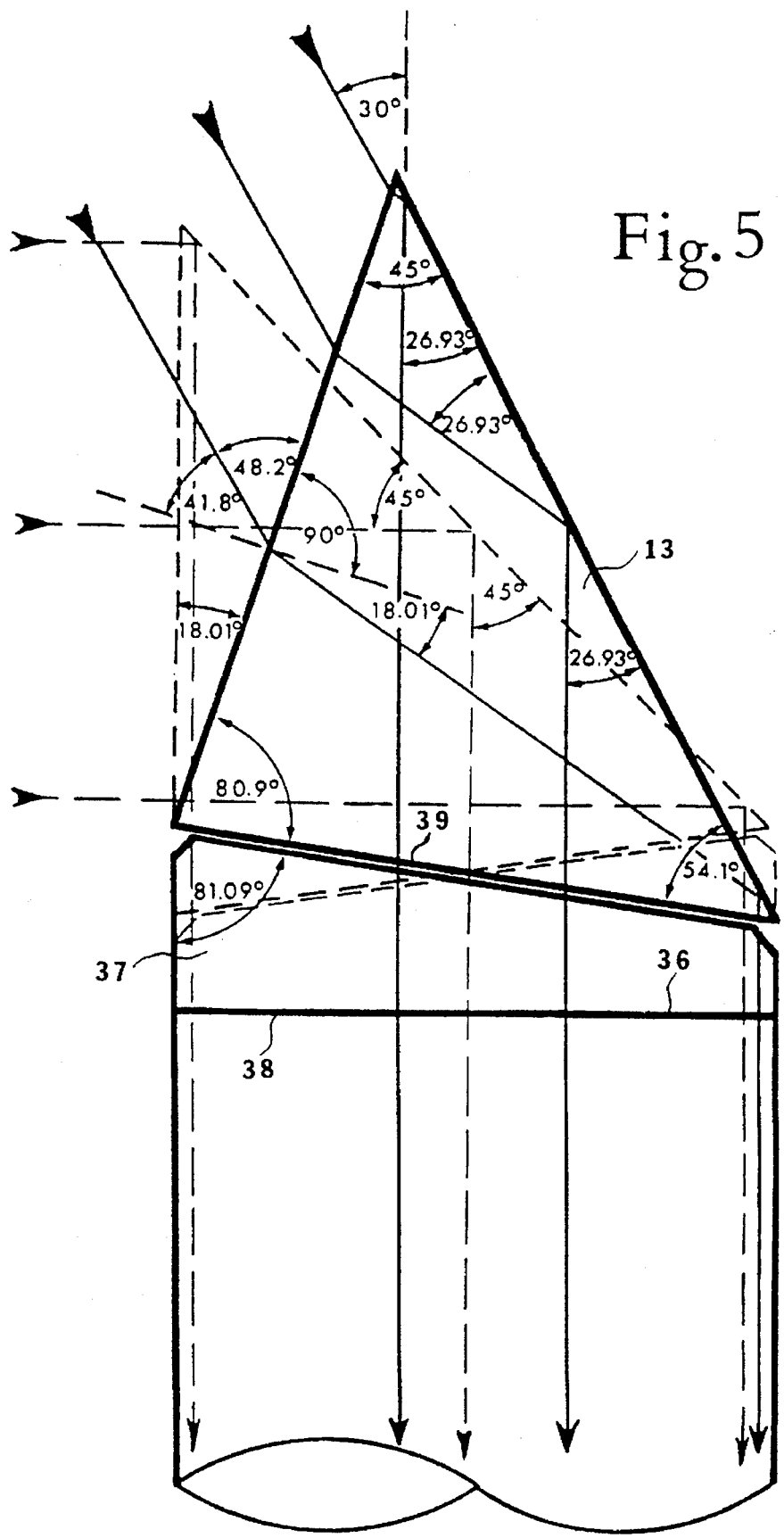
FIG. 5 is a ray diagram illustrating the passage of light from different fields of view through the prism in the embodiment of FIG. 4.

In both embodiments, the surface which engages the prism is inclined at an angle on the order of about 80° to the axis of the rod, and as illustrated in FIG. 5, the prism can be tilted between viewing angles of about 30° and 90° relative to the axis of the rod when the rod is rotated through an angle of 180°. With the prism in the position shown in full lines, light rays entering the prism at an angle on the order of 30° are directed parallel to the axis of the glass rod and the optical axis of the eyepiece. With the prism in the position shown in dashed lines, rays entering the prism at an angle of about 90° to the axis are directed to the eyepiece. The prism angles and the angles which the rays reflected parallel to the axis make relative to the faces of the prism are indicated in the figure.

In operation and use, the endoscope is inserted through a suitable opening into the body of the patient until the prism is in the area to be viewed. The outer housing is rotated about its axis to change the rotational position of the prism, and the operating ring is rotated to turn the glass rod and thereby adjust the tilt of the prism to provide the desired angle of view.

The invention has a number of important features and advantages. It provides an instrument which has a continuous, uninterrupted, homogeneous light path, and a viewing angle which can be changed without interruption of that path. In an endoscope, it provides continuous scanning for viewing and examining different features of internal cavities and hollow organs of the human body. The prism and the image guide together form a continuous uninterrupted homogeneous optical path which extends through the prism and the image guide, and the image guide rotates to tilt the prism without interruption of that path.

It is apparent from the foregoing that a new and improved endoscopic instrument has been provided. While only certain presently preferred embodiments have been described in detail, as will be apparent to those familiar with the art, certain changes and modifications can be made without departing from the scope of the invention as defined by the following claims.

I claim:

1. An endoscopic instrument comprising: an axially elongated image guide having an inclined surface at one end thereof, a prism having a surface in rotational contact with the inclined surface for directing optical images from an external field of view through the image guide, and means for rotating the image guide relative to the prism with the inclined surface of the image guide in contact with the surface of the prism to thereby tilt the prism relative to the rod and change the field of view from which images are directed through the image guide.

2. The instrument of claim 1 wherein the prism is fabricated of a material having a relatively high index of refraction, and the image guide includes a plate fabricated of the same material as the prism, the inclined surface being formed on one side of the plate.

3. The instrument of claim 2 wherein the prism and the plate are fabricated of cubic zirconia.

4. The instrument of claim 1 wherein the image guide and the prism are held together by a bellows.

5. An endoscopic instrument comprising: an axially elongated housing, an eyepiece and a prism disposed at opposite ends of the housing, the housing being adapted to be inserted through an opening in the human body with the prism inside the body and the eyepiece outside the body, an image guide within the housing for transmitting optical images from the prism to the eyepiece, an inclined surface at the end of the image guide where the prism is disposed, a bellows interconnecting the prism and the housing and maintaining a surface of the prism in contact with the inclined surface of the image guide, and means operable at the end of the housing where the eyepiece is disposed for rotating the image guide within the housing to tilt the prism to different angles for delivering images to the eyepiece from different regions within the body.

6. The instrument of claim 5 wherein the prism is fabricated of a material having a relatively high index of refraction, and the image guide includes a plate fabricated of the same material as the prism, the inclined surface being formed on one side of the plate.

7. The instrument of claim 6 wherein the prism and the plate are fabricated of cubic zirconia.

8. An endoscopic instrument comprising: an axially extending tubular housing, an image transmissive glass rod rotatively mounted within the housing with an inclined surface at one end thereof, a prism disposed at one end of the housing for directing optical images from an external field of view to the glass rod, a bellows mounting the prism to the housing with one surface of the prism in rotational contact with the inclined surface at the one end of the glass rod, an eyepiece disposed at the end of the housing opposite the prism for receiving images transmitted through the rod from the prism, and means operable at the end of the housing where the eyepiece is disposed for rotating the glass rod and the inclined surface within the housing to thereby tilt the prism and change the field of view from which images are transmitted to the eyepiece.

9. The instrument of claim 8 wherein the inclined surface is inclined at an angle on the order of 80° relative to the longitudinal axis of the glass rod.

10. The instrument of claim 8 wherein the inclined surface is formed by a plate of cubic zirconia affixed to the one end of the glass rod.

11. The instrument of claim 8 wherein the means for rotating the glass rod comprises a pin affixed to the rod and extending in a radial direction through a circumferentially extending slotted opening in the housing, and an operating ring rotatably mounted on the housing and connected to the pin.

12. An optical instrument comprising: a solid, light transmissive image guide having an inclined surface at one end thereof, a prism having a surface in rotational contact with the inclined surface for directing optical images from an external field of view through the image guide, the prism and the image guide together forming a continuous uninterrupted homogeneous optical path which extends through the prism and the image guide, and means for rotating the image guide relative to the prism without interruption of the optical path to thereby tilt the prism and change the field of view from which images are directed through the image guide.

13. The instrument of claim 12 wherein the light guide comprises an elongated body of relatively soft material with a plate of relatively hard material at one end of the body, the inclined surface being formed on one side of the plate.

14. The instrument of claim 13 wherein the prism and the plate are fabricated of cubic zirconia.

15. The instrument of claim 12 including a flexible bellows enclosing the contacting surfaces of the light guide and the prism.

* * * * *